United States Patent
Kuever et al.

(10) Patent No.: US 6,693,195 B2
(45) Date of Patent: Feb. 17, 2004

(54) PROCESS FOR PREPARING 4,6-DIHYDROXYPYRIMIDINE (DHP)

(75) Inventors: Andreas Kuever, Alfter (DE); Artur Hunds, Bonn (DE)

(73) Assignee: Degussa AG, Duesseldorf (DE)

( * ) Notice: Subject to any disclaimer, the term of this patent is extended or adjusted under 35 U.S.C. 154(b) by 22 days.

(21) Appl. No.: 10/219,542

(22) Filed: Aug. 16, 2002

(65) Prior Publication Data

US 2003/0060628 A1 Mar. 27, 2003

(30) Foreign Application Priority Data

Aug. 16, 2001 (DE) .......................... 101 40 269

(51) Int. Cl.$^7$ .......................................... C07D 239/52
(52) U.S. Cl. ...................................... 544/319
(58) Field of Search ........................ 544/319

(56) References Cited

U.S. PATENT DOCUMENTS

| | | | |
|---|---|---|---|
| 5,059,605 A | 10/1991 | Clough et al. | 514/269 |
| 5,206,245 A | 4/1993 | Clough et al. | 514/269 |
| 5,847,139 A | 12/1998 | Hunds | 544/319 |

FOREIGN PATENT DOCUMENTS

| | | |
|---|---|---|
| EP | 1200308 | 9/1965 |
| EP | 0 382 375 | 8/1990 |
| EP | 0 393 861 | 10/1990 |
| EP | 0 468 684 A2 | 1/1992 |
| EP | 0 468 695 | 1/1992 |
| EP | 0 816 345 A1 | 1/1998 |
| EP | 0 852 580 | 7/1998 |
| WO | WO 97/08152 | 3/1997 |
| WO | WO 97/44327 | 11/1997 |

OTHER PUBLICATIONS

R. Hull, Chem. Soc, P. 2214, "A New Synthesis of 4 : 6–Dihydroxypyrimidines", May 9, 1951.
C. Hennart, et al., Bull. Soc. Chim, P. 741–742, "Contribution a La Synthese De La Dichloro–4–6 Pyrimidine", 1959.
D.J. Brown, J. Chem. Soc., Pyrimidine Reactions, pp. 2312–2314, "Pyrimidine Reactions. Part I. Pyrimidines from Malondiamide", 1956.

*Primary Examiner*—John M. Ford
(74) *Attorney, Agent, or Firm*—Oblon, Spivak, McClelland, Maier & Neustadt, P.C.

(57) ABSTRACT

The invention relates to a process for the preparation of 4,6-dihydroxypyrimidine by reaction of malonic ester with formamide and alkali metal alkoxide. The malonic ester is added alone or simultaneously with the total quantity or a portion of the formamide, in portions or continuously with monitoring of the temperature, to the alkali metal alkoxide prepared as a solution or suspension in an alcohol, alone or together with the total quantity or remaining quantity of the formamide. A temperature of from 102 to <120° C. is then set for from 10 to <60 minutes. The work-up after the holding time in said temperature range is then carried out by methods known per se.

40 Claims, No Drawings

PROCESS FOR PREPARING 4,6-DIHYDROXYPYRIMIDINE (DHP)

CROSS-REFERENCE TO RELATED APPLICATION

This application claims priority to German Patent Application 10140269.4, filed Aug. 16, 2001, which is hereby incorporated by reference in its entirety.

BACKGROUND OF THE INVENTION

1. Field of the Invention

A process for preparing 4,6-dihydroxypyrimidine ("DHP", "4,6-DHP", also known as 1-H-pyrimidine-4,6-dione in its tautomeric form) from malonic ester, formamide and alkali metal alkoxide. DHP has the following structure:

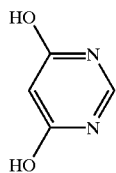

DHP is a useful intermediate for the syntheses of active ingredients. For instance, DHP, 4,6-dihydroxypyrimidine be used to prepare the corresponding dichloropyrimidine which, in turn, may be processed to give novel, highly active fungicides (EP-A-0 382 375, 0 393 861, 0 468 684 and 0 468 695).

2. Description of Related Art

Most of the known processes for the preparation of 4,6-dihydroxypyrimidine start from malonamide and react this with ethyl formate, see, for example, R. Hull, J. Chem. Soc., 1951, 2214 and C. Hennart and E. Merlin, Bull. Soc. Chem., 1959, 741. Reaction of malonamide with formamide also provides a known route to DHP, see D. J. Brown, J. Chem. Soc., 1956, 2312–2314 and A. Sömmer, DE-A-12 00 308, or V. A. Zasonov, Khim.-Farm. Zh., Vol. 8, No. 12, 28–31. In Zasonov, the malonamide is formed before the cyclocondensation reaction between malonic ester and ammonia. The amide is isolated before further use.

The common disadvantage of all processes starting from malonamide is that the amide cannot be commercially obtained and that nitrogen sources are not used efficiently in multistep preparation processes for DHP, because losses occur in the individual steps. This criticism extends to the process described by EP-A 0 852 580 (Lonza AG), which discloses an elegant route to malonamide and malonic monoamide monoester, but the above-recited disadvantages apply to their further reaction with formamide.

EP-A-0 816 345 teaches that DHP can be synthesised by reacting the malonic ester, formamide and the alkoxide with each other in one step under increased temperature and autogenous pressure, which gives DHP in good yields, very good space-time yields and high degrees of utilisation of the nitrogen source formamide. Therefore, the process described in EP-A-0 816 345 constitutes a distinct advance in the art. In particular, the integrated dissolution of the alkali metal salt of DHP obtained as an intermediate and the isolation of the solid which only takes place in the last step make the process additionally advantageous.

However, the process described by EP-A-0 816 345 also has certain disadvantages, including the need for long addition and post-reaction times and poor product yields when commercially available alkoxides, such as NM30, are used. For instance, the yields achievable using the commercially available 30% solution of sodium methoxide in methanol (NM30) are up to 9% lower than those achievable by using more highly concentrated methoxide solutions according to the examples of EP-A-0 816 345. Therefore, from the perspective of obtaining a more efficient and economical process, it would be advantageous to shorten the addition and reaction times, as well as improve yields of the process when using commercially available reactants.

BRIEF DESCRIPTION OF THE INVENTION

One object of the present invention is to provide a process for the preparation of 4,6-dihydroxpyrimidine without the above-described disadvantages. Thus, the invention provides a process for the preparation of 4,6-dihydroxypyrimidine (DHP) from malonic ester, formamide and alkali metal alkoxide. This process was surprisingly found to give a significant increase in the yield compared to the above-described prior art processes.

The invention also provides a process that reduces cyanide content produced by the reaction, and thus reduces entrainment of cyanide in waste water and reduces environmental and occupational risks as cyanides and hydrocyanic acid formed by acidification are highly toxic.

DETAILED DESCRIPTION OF THE INVENTION

In the inventive process, the temperature is held in the range from 102 to <120° C. from 10 to <60 minutes after mixture or proportioning of the substrates. Any subrange or intermediate temperature within this range may also be used, such as 102–104° C., 104–106° C., 106–108°C., 108–110° C., 110–112° C., 112–114° C., 114–116°C., 116–118° C. or 118 to <120° C. Similarly any intermediate period between 10 and <60 minutes may be used, such as 10–20, 20–30, 30–40, 40–50 or 50 to <60 minutes may be used. The exact holding time depends on the particular temperature employed after completion of the mixture or the metered addition of substrate(s). A metered addition can be carried out, provided heat is removed sufficiently well, in preferably 10–50 minutes, in particular from 10 to 30 minutes and more preferably in about 20 minutes Moreover, a surprising strong correlation between holding time, temperature, reaction time and yield achieved was found. For instance, a comparative investigation at the temperatures 90° C., 105° C. and 120° C. and a reaction time of 30 minutes gave a virtually inverse parabolic function for the yield with a maximum at about 105° C. Thus, it has been found that the metered addition or proportioning of substrates, as well as the holding time and temperature after metered addition or proportioning, provided by processes of the invention are important variables for obtaining superior yields.

Production standards for 4,6-DHP require that certain specifications be met and that particular secondary components be kept below a particular maximum permitted concentration. The process of the present invention facilitates production of "on-spec" product, and in high yields.

An "on-spec" product may meet one or all of the following requirements:

Determination of concentration by potentiometric titration (pH electrode) with potassium hydroxide solution (internal method). Requirement >96%.

Product purity by reverse-phase HPLC (RP 18), gradient elution (aqueous ammonium acetate solution/ acetonitrile) with UV detection (300 nm) (internal method). Requirement <0.8% total impurities.

Malonic acid diamide by GC with FID (internal method). Requirement <0.45%.

For instance, a comparative process for the production of 4,6-DHP, that operates at a reaction temperature of 90° C. and a reaction time of 1 hour provides only an 82% yield of on-spec product—see Comparative Example 1. This product is characterised by the DHP content determined by potentiometric titration being ≧96%, and the quantity of the component 2,4,6-trihydroxynicotinamide determined by a stipulated HPLC method being given by a certain relative peak area.

On the other hand, the process of the invention eliminates the described disadvantages in such a way that at a temperature of from 102 to <120° C., preferably from 103 to 115° C. and more preferably from 103 to 107° C., and a holding time of from 10 to <60 minutes, preferably from 20 to 40 minutes and more preferably from about 25 to 35 minutes (operating point of 30 minutes) a product is obtained in increased yield that is additionally impeccable with regard to described specifications and that is obtained in a considerably shorter total cycle time compared to the standard process—see Example 1. It was surprisingly found that the time after completion of the metered addition (holding time) in the given temperature range must absolutely be adhered to.

Preferable alkali metal alkoxides are sodium or potassium alkoxides, in particular sodium alkoxides. The alcoholic radical in the alkoxide contains from 1 to 4, preferably from 1 to 2, more preferably 1 carbon atom, i.e. preferably the methyl or ethyl group. The use of sodium methoxide is most preferred.

An additional condition to be considered is that the amount of cyanide, which can be formed by decomposition of formamide, should be as low as possible in the alkaline phase before precipitation, in order to avoid entrainment of hydrogen cyanide (HCN) into the wastewater and/or sections of the plant for the precipitation, filtration and drying. The process described above where a relatively short holding time is used gives a tolerable cyanide content of only [CN$^-$]≦5 ppm in the alkaline phase before filtration.

Further investigations have shown that although operation of the process at 120° C. for 20 minutes again gave the stated increases in yield and space-time yield, the material obtained was marginally off-spec (see Comparative Example 2). In this respect, it was found that using the operating range of from 10 to <60 minutes at from 102 to <120° C., in particular 25 to 35 minutes at 103 to 107° C. and more preferably 30 minutes at 105° C., a surprising increase in the yield and purity, and therefore also the productivity, relative to the standard process is achieved. The described strong correlation between time and temperature becomes even more clear when results are considered that were achieved by operating the reaction for 30 minutes at 120° C. (see Comparative Example 3): the yields fell below the standard.

Furthermore, it was surprisingly found that the described correlations between temperature and time can be employed with great advantage in systems operated using non-commercially obtainable, more highly concentrated sodium methoxide (NM). In particular, the use of a methoxide solution or suspension in methanol, which can be prepared by incipient distillation of the commercial material NM30 in the reaction vessel, having a concentration of from 33 to 45% by weight appears to be advantageous, a concentration in the range from 33 to 37% by weight to be more advantageous, and a concentration of 35% by weight (NM35) to be most advantageous. It can be seen from Inventive Example 2 and Comparative Examples 4 and 5 that the use of NM35 gives a further increase in yield, and the described strong temperature-time correlation applies as before. A similar statement applies to the use of a 40% by weight methoxide solution or suspension, which results in a further increase in yield, but whose use does not necessarily appear to be more economical overall. Metered addition of the reactants can be carried out so that the malonic ester is added alone or simultaneously with the total quantity or a portion of the formamide, in portions or continuously, to the alkali metal alkoxide prepared as a solution or suspension in an alcohol, alone or together with the total quantity or the remaining quantity of the formamide.

The actual reaction of the malonic ester with the formamide takes place by a method known per se, customarily in the range from 20 to 80° C. (see inventive examples).

The malonic ester preferably contains alkyl groups having from 1 to 4 carbon atoms.

Furthermore, it was most surprisingly found that 20 minutes are normally completely sufficient for the metered addition of the malonic ester and thus considerable shortening of the total process time can be achieved without further disadvantages compared to the process described in EP-A-0 816 345.

After completion of the holding time, the work-up of the reaction mixture is carried out by methods known per se, customarily by depressurising to atmospheric pressure, admixing with water, setting the pH value and removing the precipitated salt by a mechanical separating operation such as filtration, decantation or centrifugation, and washing and drying it, see inventive examples.

The examples, which follow, illustrate the invention, however, but the invention is not limited to the processes described in these examples.

EXAMPLES

Inventive Example 1

A 2 l autoclave with rotating stirrer is charged with 3.3 mol of sodium methoxide in methanol (NM30) and 2.25 mol of formamide. The mixture is heated to from 50 to 55° C. The pressure in the autoclave ranged from 1 to 6 bar gauge. 1 mol of dimethyl malonate is then pumped in within 20 minutes, and the mixture remains below 65° C. After completed addition, the temperature is set at 105° C. for 30 minutes, then the autoclave is depressurised and purged with nitrogen. 460 ml of deionized water are then added to the reaction mixture. About 300 g of aqueous 36% by weight hydrochloric acid are then added dropwise with cooling, monitoring of the pH and holding of the temperature between 20 and 25° C. The precipitated DHP is filtered off with suction and washed three times with water. After drying at from 70 to 80° C. and 20 to 30 mbar, 94.83 g of on-spec DHP, corresponding to a yield of 84.6% of the theory, are obtained.

Inventive Example 2

A 2 l autoclave with rotating stirrer is charged with 3.3 mol of sodium methoxide in the form of NM35 and 2.25 mol of formamide. The mixture is heated to from 50 to 55° C. 1 mol of dimethyl malonate is then pumped in within 20 minutes, and the mixture remains below 65° C. After completed addition, the temperature is set at 105° C. for 30 minutes, then the autoclave is depressurised and purged with nitrogen. Deionized water is then added to the mixture and it is worked up as described in Example 1. After drying at from 70 to 80° C. and 20 to 30 mbar, 96.96 g of on-spec DHP, corresponding to a yield of 86.5% of the theory, are obtained.

Comparative Example 1

The process is carried out as described in Inventive Example 1, except that the temperature is set to 90° C. for 60 minutes after completed addition. Only 91.35 g of on-spec DHP, corresponding to a yield of 81.5% of the theory, are obtained.

Comparative Example 2

The process is carried out as described in Inventive Example 1, except that the temperature is set to 120° C. for 20 minutes after completed addition. 94.27 g of off-spec DHP (peak area in HPLC purity test too large), corresponding to a yield of 84.1% of the theory, are obtained.

Comparative Example 3

The process is carried out as described in Inventive Example 1, except that the temperature is set to 120° C. for 30 minutes after completed addition. 90.23 g of on-spec DHP are obtained. However, the yield is only 80.5% of the theory.

Comparative Example 4

The process is carried out as described in Inventive Example 2, except that the temperature is set to 90° C. for 60 minutes after completed addition. 92.92 g of on-spec DHP are obtained. However, the yield is only 82.9% of the theory.

Comparative Example 5

The process is carried out as described in Inventive Example 2, except that the temperature is set to 120° C. for 30 minutes after completed addition. 95.95 g of off-spec DHP, corresponding to a yield of 85.6% of the theory, are obtained.

engineering, biochemical arts or in related fields are intended to be within the scope of the following claims.

Incorporation by Reference

Each document, patent, patent application or patent publication cited by or referred to in this disclosure is incorporated by reference in its entirety. However, no admission is made that any such reference constitutes prior art and the right to challenge the accuracy and pertinence of the cited documents is reserved. Specifically, priority document DE (Germany) 10140269.4, filed Aug. 16, 2001 is hereby incorporated by reference.

We claim:

1. A process for preparing 4,6-dihydroxypyrimidine (DHP) comprising mixing malonic ester with formamide and an alkali metal alkoxide to form a mixture, and
holding said mixture at a temperature ranging from 102 to <120° C. for a holding time ranging from 10 to <60 minutes.

2. The process of claim 1, wherein the reactants are mixed by the metered addition of one or more reactant(s) to the mixture.

3. The process of claim 2, wherein the metered addition takes from 10 to 50 minutes.

4. The process of claim 1, comprising the metered addition of malonic ester or formamide, or both, to a solution comprising an alkali metal alkoxide.

5. The process of claim 1, wherein the malonic ester is added alone to the alkali metal alkoxide, followed by addition of the formamide.

6. The process of claim 1, wherein the malonic ester and at least a portion of the formamide is added to the alkali metal alkoxide, followed by the addition of any remaining formamide.

7. The process of claim 1, wherein the malonic ester or the formamide, or both, are continuously added to the alkali metal alkoxide.

8. The process of claim 1, wherein the malonic ester of the formamide, or both are added at intervals to the alkali metal alkoxide.

9. The process of claim 1, wherein the alkali metal alkoxide is provided as a solution or suspension in an alcohol.

TABLE I

|  | Invention | | Comparative Example | | | | |
| --- | --- | --- | --- | --- | --- | --- | --- |
|  | 1 | 2 | 1 | 2 | 3 | 4 | 5 |
| NsMeth | NM30 | NM35 | NM30 | NM30 | NM30 | NM35 | NM35 |
| Temperature after addition | 105 | 105 | 90 | 120 | 120 | 90 | 120 |
| Time | 30 | 30 | 60 | 20 | 30 | 60 | 30 |
| Yield | 94.83 | 96.96 | 91.35 g | 94.27 | 90.23 | 92.92 | 95.95 |
| On-spec | yes | yes | yes | no | yes | yes | no |
| th yield | 84.6 | 86.5 | 81.5% | 84.1 | 80.5 | 82.9 | 85.6 |

Modifications and other Embodiments

Various modifications and variations of the described methods and products, as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the chemical, chemical 10. The process of claim 1, wherein the alcohol is methanol.

11. The process of claim 1, wherein the malonic ester contains alkyl groups having 1 to 4 carbon atoms.

12. The process of claim 1, wherein the alkoxide comprises an alkyl radical having 1 to 4 carbon atoms.

13. The process of claim 1, wherein the aliphatic radical in the alkoxide is methyl or ethyl.

14. The process of claim 1, wherein the alkoxide is a sodium or potassium alkoxide.

15. The process of claim 1, wherein the alkali metal alkoxide is a 30% solution of sodium methoxide in methanol (NM30).

16. The process of claim 1, wherein the alkali metal alkoxide is >30% solution of sodium methoxide in methanol.

17. The process of claim 1, wherein the alkali metal alkoxide is a 33–45% solution of sodium methoxide in methanol.

18. The process of claim 1, wherein the alkali metal alkoxide is a 33–37% solution of sodium methoxide in methanol.

19. The process of claim 1, wherein the holding time ranges from 10 to 20 minutes.

20. The process of claim 1, wherein the holding time ranges from 20 to 30 minutes.

21. The process of claim 1, wherein the holding time ranges from 30 to 40 minutes.

22. The process of claim 1, wherein the holding time ranges from 40 to 50 minutes.

23. The process of claim 1, wherein the holding time ranges from 50 to <60 minutes.

24. The process of claim 1, wherein the reaction temperature ranges from 102 to 104° C.

25. The process of claim 1, wherein the reaction temperature ranges from 104 to 106° C.

26. The process of claim 1, wherein the reaction temperature ranges from 106 to 108° C.

27. The process of claim 1, wherein the reaction temperature ranges from 108 to 110° C.

28. The process of claim 1, wherein the reaction temperature ranges from 110 to 112° C.

29. The process of claim 1, wherein the reaction temperature ranges from 112 to 114° C.

30. The process of claim 1, wherein the reaction temperature ranges from 114 to 116° C.

31. The process of claim 1, wherein the reaction temperature ranges from 116 to 118° C.

32. The process of claim 1, wherein the reaction temperature ranges from 118 to <120° C.

33. The process of claim 1, wherein the mixture is set to a temperature ranging from about 103° C. to about 107° C. and the holding time ranges from about 25 to 35 minutes.

34. The process of claim 1, wherein the mixture is set to a temperature of about 105° C. and the holding time is about 30 minutes.

35. The process of claim 1, wherein the reaction is carried out using from 33 to 37% by weight sodium methoxide solution or suspension in methanol, the temperature is set to from 103° C. to 107° C. after completion of a metered addition of malonic ester and/or formamide, and the holding period for the mixture at this temperature following said metered addition ranges from 25 to 35 minutes.

36. The process of claim 1, further comprising recovering the DHP in the mixture after completion of the holding time.

37. The process of claim 36, wherein the mixture remaining after recovery of the DHP contains no more than 5 ppm of cyanide.

38. The process of claim 1, further comprising precipitating the DHP in the mixture, and recovering the precipitated DHP by filtration, decantation and/or centrifugation, and optionally washing and/or drying the precipitated DHP.

39. The process of claim 1, further comprising after completion of the holding time, adding water to the mixture and adjusting the pH and/or temperature of the mixture to precipitate DHP.

40. The process of claim 1, wherein the reaction mixture has a cyanide content no more than 5 ppm.

* * * * *